(12) United States Patent
Kurukchi et al.

(10) Patent No.: US 10,065,909 B2
(45) Date of Patent: *Sep. 4, 2018

(54) REMOVAL OF CARBONYLS FROM GASEOUS HYDROCARBON STREAMS

(71) Applicant: Janus Technology Solutions, LLC, The Woodlands, TX (US)

(72) Inventors: Sabah A. Kurukchi, Houston, TX (US); Joseph M. Gondolfe, Magnolia, TX (US)

(73) Assignee: Janus Technology Solutions, LLC, The Woodlands, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 15/805,828

(22) Filed: Nov. 7, 2017

(65) Prior Publication Data

US 2018/0057426 A1    Mar. 1, 2018

Related U.S. Application Data

(63) Continuation of application No. 15/231,524, filed on Aug. 8, 2016, now Pat. No. 9,834,498.

(60) Provisional application No. 62/207,729, filed on Aug. 20, 2015.

(51) Int. Cl.
  $C07C\ 11/06$       (2006.01)
  $C07C\ 7/00$        (2006.01)
  $C07C\ 7/148$       (2006.01)
  $C07C\ 9/08$        (2006.01)

(52) U.S. Cl.
  CPC .............. $C07C\ 7/005$ (2013.01); $C07C\ 7/148$ (2013.01); $C07C\ 7/14858$ (2013.01); $C07C\ 9/08$ (2013.01); $C07C\ 11/06$ (2013.01)

(58) Field of Classification Search
  None
  See application file for complete search history.

(56) References Cited

U.S. PATENT DOCUMENTS

| | | | | |
|---|---|---|---|---|
| 2,456,692 A | * | 12/1948 | Farkas | C07F 9/06 |
| | | | | 508/317 |
| 2,457,257 A | * | 12/1948 | Michael | C07C 45/85 |
| | | | | 518/717 |
| 2,568,517 A | * | 9/1951 | Sharp | C07C 29/86 |
| | | | | 518/717 |
| 2,625,560 A | * | 1/1953 | Michael | C07C 45/80 |
| | | | | 518/723 |

(Continued)

OTHER PUBLICATIONS

Dissociation of Aldehyde Bisulfite Compounds by T.D. Stewart et al, dated Jun. 6, 1932.

(Continued)

*Primary Examiner* — Tam M Nguyen
(74) *Attorney, Agent, or Firm* — Tumey L.L.P

(57) ABSTRACT

Disclosed are methods and systems for removing a highly reactive polymer precursor such as acetaldehyde and acetone from a hydrocarbon gas stream. Embodiments may disclose a method for removal of carbonyls comprising providing a hydrocarbon gas stream comprising a carbonyl, providing a liquid bisulfite stream, and contacting the hydrocarbon gas stream and liquid bisulfite stream in a mass transfer device wherein at least a portion of the carbonyl reacts with the bisulfite to form a solid adduct that is soluble in the liquid bisulfite stream.

19 Claims, 3 Drawing Sheets

(56) References Cited

U.S. PATENT DOCUMENTS

| | | | | |
|---|---|---|---|---|
| 2,691,669 A | * | 10/1954 | Walker | C07C 27/22 518/723 |
| 3,816,478 A | | 7/1974 | Washall | |
| 3,829,379 A | * | 8/1974 | Ishida et al. | B01D 53/72 210/626 |
| 4,125,568 A | * | 11/1978 | Theriot | C07C 7/152 585/834 |
| 4,409,375 A | | 10/1983 | Hartman | |
| 4,673,489 A | | 6/1987 | Roling | |
| 4,952,301 A | | 8/1990 | Awbrey | |
| 5,150,425 A | | 9/1992 | Martin et al. | |
| 5,160,425 A | | 11/1992 | Lewis | |
| 5,194,143 A | | 3/1993 | Roling | |
| 5,220,104 A | | 6/1993 | McDaniel et al. | |
| 5,264,114 A | | 11/1993 | Dunbar | |
| 5,582,808 A | * | 12/1996 | Patek | C10G 19/02 208/48 AA |
| 5,714,055 A | | 2/1998 | Lewis | |
| 6,037,516 A | * | 3/2000 | Morford | C07C 7/148 208/256 |
| 8,722,954 B2 | | 5/2014 | Bauchet | |
| 2014/0114104 A1 | * | 4/2014 | Caranoni | C10G 9/26 585/303 |
| 2015/0139878 A1 | * | 5/2015 | Tanaka | B01D 53/62 423/228 |
| 2015/0353439 A1 | * | 12/2015 | Van Westrenen | C07C 4/04 585/302 |

OTHER PUBLICATIONS

USPTO Notice of Allowance for U.S. Appl. No. 15/231,524 dated Aug. 15, 2017.

USPTO Final Office Action for U.S. Appl. No. 15/231,524 dated Jun. 21, 2017.

USPTO First Action Interview—Office Action for U.S. Appl. No. 15/231,524 dated May 30, 2017.

* cited by examiner

REMOVAL OF CARBONYLS FROM GASEOUS HYDROCARBON STREAMS

BACKGROUND

Base petrochemicals such as olefins are largely produced in steam cracking plants using saturated aliphatic hydrocarbon feedstocks, such as ethane, propane, or higher molecular weight hydrocarbon mixtures such as naphtha, atmospheric and/or vacuum gas oils, and the like, at high temperatures (e.g. >800 C) in the presence of steam to crack the saturated hydrocarbon molecules to lower molecular weight unsaturated hydrocarbons such as ethylene predominately, followed by propylene, and then various quantities of $C_4$, $C_5$ and $C_6$ mono- and diolefinic hydrocarbons, with a lesser quantity of $C_7$ and higher weight saturated and unsaturated aliphatic, cyclic and aromatic hydrocarbons.

In steam cracker plants, it is common to remove acid gas components, such as carbon dioxide ($CO_2$) and hydrogen sulfide ($H_2S$), from hydrocarbon gas streams by intimate contact with an aqueous solution of a strong base such as sodium hydroxide (NaOH), typically referred to as a caustic solution. By reaction with the caustic contained in solution, i.e. NaOH, acid gas components such as hydrogen sulfide and carbon dioxide are converted into sodium sulfide ($Na_2S$), sodium hydrosulfide (NaHS), sodium carbonate ($Na_2CO_3$) and sodium bicarbonate ($NaHCO_3$) which are absorbed into the caustic solution and, thus, removing these acid gases from the hydrocarbon stream.

During steam cracking any sulfur containing compounds added and/or present in the hydrocarbon feed stream may be converted into hydrogen sulfide and/or organically bound sulfur compounds, and also, a content of carbon dioxide may be generated by a water-gas shift reaction. The resultant gas mixture from steam cracking may then be quenched from a temperature of about 700-1100° to a lower temperature of about 35 to 40° C. whereupon the major portion of its water and $C_7$+ hydrocarbon content may be condensed and separated from the gas mixture. After quenching, the remaining constituents of the gas mixture may be conditioned by various steps of gas compression and refrigerative cooling to prepare it for cryogenic distillation whereby its ethylene, propylene and butenes contents will ultimately be recovered in essentially pure form for ultimate use as monomers in the production of various polymers, such as polyethylene, ethylene copolymers, polypropylene and the like.

One step required to properly condition the gas mixture prior to its cryogenic distillation is to scrub the cracked gas essentially free of any acid gas components, such as hydrogen sulfide and carbon dioxide. This is accomplished at some interstage location of a multi-stage gas compression system and, on occasion post-compression, wherein the cracked gas stream is at a pressure of from about 10 to about 20 atmospheres (atm) by contacting the compressed gas stream with an aqueous sodium hydroxide solution by countercurrent contact in a gas-liquid contact vessel often referred to as an "absorber," "Caustic Scrubber" or "Caustic Tower." After such gas scrubbing contact the aqueous sodium hydroxide solution which is discharged from the bottom of this tower contains, in addition to some unreacted sodium hydroxide, sodium sulfide, sodium hydrosulfide, sodium carbonate and sodium bicarbonate that results from the removal of acid gas compounds from the so scrubbed gas stream. To prevent a build-up of the concentration of these components in the caustic tower and to provide for hydraulic room to add a quantity of fresh higher strength caustic solution to the caustic tower to make up for the consumption of caustic therein, a quantity of this weak or "tower spent" caustic solution is bled away from being recirculated back to the tower. However, to maintain a proper liquid volume of caustic solution circulation within the tower, a portion of this weak or "tower spent" caustic solution is recirculated back to the tower. That quantity of weak or "spent" caustic solution which is bled away from the tower has been referred to in this art as "spent caustic." Such tower spent caustic has to be conditioned by further processing steps in a spent caustic treatment unit to condition it as environmentally acceptable by industry standards.

The caustic tower can be an important factor in determining the production capacity of an ethylene production unit because it is necessary to remove acid gas components so that the scrubbed hydrocarbon gas has a minimal, acceptable level of these components. Further, since the majority of the cracked gas must pass through the caustic tower, if the caustic tower reaches its capacity limit, then the caustic tower can establish an equipment limit for ethylene production. Thus, the capacity of the caustic tower can be an important factor in determining the capacity of the ethylene production unit, regardless whether the ethylene production unit is being designed for grassroots construction or is an already existing facility.

Steam cracking of hydrocarbons also produces small quantities of oxygenated compounds, carboxylic acids, phenols and carbonyls, mainly acetaldehyde. Carboxylic acids and phenols are removed in the quench water tower due to their high solubility in the aqueous phase.

In an acid gas removal system, amine absorber and caustic tower, some of the oxygenated compounds are also removed. It is known in the art of hydrocarbon processing that some of these oxygenated compounds, especially carbonyl compounds and particularly acetaldehyde, will undergo polymerization in the presence of a strong base such as caustic solution. When removing acid gases with amine or caustic, aldehydes are trapped. The aldehydes in the caustic solutions reacts producing polyaldols by Aldol Condensation Reaction(s). These polymers, known in the industry as "red oil", induce fouling of the amine absorber and/or the caustic scrubber. Aldol Condensation Reactions result the liquid red oil formation, which is a reaction product of few numbers of aldehyde monomer, and further polymerization leads to the formation of high molecular weight red/yellow solid polymer. In the AGR system, the acetaldehyde polymer will settle on internal equipment surfaces leading to fouling and eventual plugging. Fouling and plugging of the internal equipment means the unit must be shut down to perform cleaning. Every time a unit operation has to be shut down for cleaning it means that a cost is incurred due to lost production, over and above, the actual cost to clean the equipment.

Steam crackers also produce smaller quantities of light aromatics (benzene, toluene, and xylene) that are found to help dissolve and disperse the Aldol polymer formed. And it became an industry practice to introduce a solvent, advantageously benzene or toluene or xylenes, in the caustic scrubber and/or in the alkaline solution fed to the scrubber to reduce the formation of the fouling deposits by reducing red oil formation and not only by the dissolution of them.

Also, during the production of ethylene and propylene with oxygenated feedstock, such as Methanol to Olefins (MTO) and alcohol dehydration, aldehydes and carbon dioxide are produced. The amount of aldehydes produced in these processes is very high compared to the steam cracker. The other characteristic of these processes is that very low quantities of aromatics such as benzene are produced. As the concentration of aldehydes is very high, the fouling potential is excessive. In the caustic scrubber operating with the effluent of a steam cracker the presence of aromatics helps to reduce red oil fouling. On the contrary in the caustic scrubber operating with the effluent of MTO or alcohol dehydration, there are two drawbacks:

(i) There are more aldehydes, as a consequence the red oil may be increased,
(ii) There are much less aromatic byproducts, as a consequence the red oil may not be dissolved and the fouling may increase.

The capacity of a caustic tower can be, and frequently is, adversely affected by polymer formation. The cracked gas contains highly reactive carbonyls and diolefins, which can form polymers, and thus are of concern throughout the plant, but particularly in the caustic tower. The highly reactive carbonyls and diolefins, and possibly other compounds, react or polymerize to form polymers which coat, foul and plug the internals of equipment, such as the caustic tower, which reduces the equipment's efficiency and capacity and, at times, necessitates a shutdown of the equipment for cleaning. Polymer formation in the caustic tower thus reduces its capacity both by reducing its operating efficiency and by necessitating the shutdown of the caustic tower for cleaning and removing deposits of polymeric material.

The spent caustic solution leaving the caustic tower contains, in addition to sodium hydroxide, sodium sulfide, sodium hydrosulfide, sodium carbonate and sodium bicarbonate that results from the removal of acid gas compounds from the so scrubbed gas stream and also a significant content of dissolved mono- and di-olefinic hydrocarbons as well as carbonyls and other organic contaminants. In this condition, the spent caustic solution presents various problems with respect to either its environmental disposal or to its reconditioning for subsequent uses. For example, polymers tend to form in the spent caustic solution as long as the solution contains dissolved polymer precursors at an elevated temperature. Aldol condensation of dissolved oxygenated hydrocarbons (carbonyls, such as aldehydes and ketones) produces red oil polymeric products, which is and remains partially soluble in a spent caustic solution that issues from the caustic scrubbing tower. Certain highly unsaturated hydrocarbons in the cracked gas, such as acetylenes and dienes (diolefinic hydrocarbons), that pass into the spent caustic solution in the scrubbing tower may polymerize to various degrees. Liquid red oil formation, which is a product of aldol condensation of few numbers of aldehyde monomer, and further polymerization leads to the formation of high molecular weight red solid polymer. The insoluble polymeric species in the spent caustic solution precipitate out of solution and may be removed in a deoiling drum. In any event, the spent caustic solution removed from the gas scrubbing tower, even following a deoiling drum treatment, includes in dissolved form a content of such condensation and addition types of polymer and polymeric species which may later precipitate from the spent caustic solution as foulants on equipment surfaces when subsequently exposed to the spent caustic solution.

From a disposal standpoint, sodium sulfide, sodium hydrosulfide contaminants as well as the dissolved hydrocarbon and other organic contaminants impart to the spent caustic solution too high a chemical oxygen demand (COD) and/or biological oxygen demand (BOD) to allow for its environmentally acceptable disposal. Further, the alkaline value of the spent caustic stream is not useable for other purposes due to the presence therein of these contaminant components. From either perspective, the constituents of the spent caustic solution that are other than sodium hydroxide and water are contaminants which either renders it unusable or disposable absent any other further treatment.

SUMMARY

Embodiments may disclose a method for removal of carbonyls within steam cracking plants using a liquid bisulfite stream. The carbonyls may be removed by contacting the hydrocarbon gas stream and liquid bisulfite stream in a mass transfer device wherein at least a portion of the carbonyl reacts with the bisulfite to form a solid adduct that is soluble in the liquid bisulfite stream. Other embodiments may comprise a system for removal of carbonyls, wherein the system may comprise a hydrocarbon gas stream comprising a carbonyl, a liquid bisulfite stream, and a mass transfer device configured to contact the hydrocarbon gas stream and the liquid bisulfite stream.

BRIEF DESCRIPTION OF THE DRAWINGS

These drawings illustrate certain aspects of some of the embodiments of the present invention and should not be used to limit or define the invention.

DETAILED DESCRIPTION

The present invention provides a process for removing a highly reactive polymer precursor as acetaldehyde from a sour hydrocarbon gas stream (e.g. comprising $CO_2$ and $H_2S$). The polymer precursor may be removed, for example, upstream of any Acid Gas Removal (AGR) system typically using an absorber with either an amine solution, but more typically using an absorber with a caustic soda solution often referred to as a Caustic Scrubber or Caustic Tower. The benefits of the process may be the reduction (and potentially elimination of substantially all) of the formation of "red oil" formed as a consequence of Aldol Condensation Reactions from carbonyl species, most especially acetaldehyde, within the given applications. Prior to admission of the hydrocarbon gas stream to the amine absorber or caustic tower, an aqueous solution of an alkali metal bisulfite (AMBS) may be contacted counter-currently with the hydrocarbon gas stream in a packed or trayed column to remove the acetaldehyde by reacting it with the alkali metal bisulfite to form an adduct. Examples of suitable alkali metal bisulfites that may be used include, without limitation, sodium bisulfite, potassium bisulfite, other alkali metal bisulfites, and combinations thereof.

The hydrocarbon gas stream may also be mixed with the AMBS solution in a high-shear mixer, such as an inline, co-current flow static mixer or a venturi scrubber; or alternatively the hydrocarbon gas stream may be contacted with an AMBS wash section in the bottom of the Caustic Tower. The bottoms section may be about 4 or 5 trays at the bottom of the Caustic Tower. Acetaldehyde may be absorbed into and may react with the AMBS solution to form a heavy adduct that is soluble in the aqueous phase, thereby reducing (and potentially eliminating) the presence of acetaldehyde in the hydrocarbon gas stream before its admission to the AGR System.

Thus, in accordance with example embodiments, fouling of the amine absorber and caustic tower may be drastically reduced; the rich amine solution from the amine absorber may be essentially free of the polymer precursors, carbonyls, and the spent caustic may contain sodium salts (hydroxide, carbonate, bicarbonate, sulfide, and bisulfide) as well as dissolved gases to the limit of their solubility of the gaseous hydrocarbon stream. In some embodiments, the reduction (and potentially) absence of red oil polymer precursors and solid polymer may make it possible to strip the formed spent caustic of its dissolved hydrocarbon gases and obtain "pretreated" spent caustic that may comprise a solution of sodium salts.

The depleted AMBS solutions containing the acetaldehyde adduct may be regenerated by heating the solution to a temperature of 100° C. or higher, whereby the acetaldehyde adduct dissociates to acetaldehyde and AMBS. The solution is then stripped to remove the acetaldehyde and the regenerated solution can be readily recycled for reuse.

Figure 1:
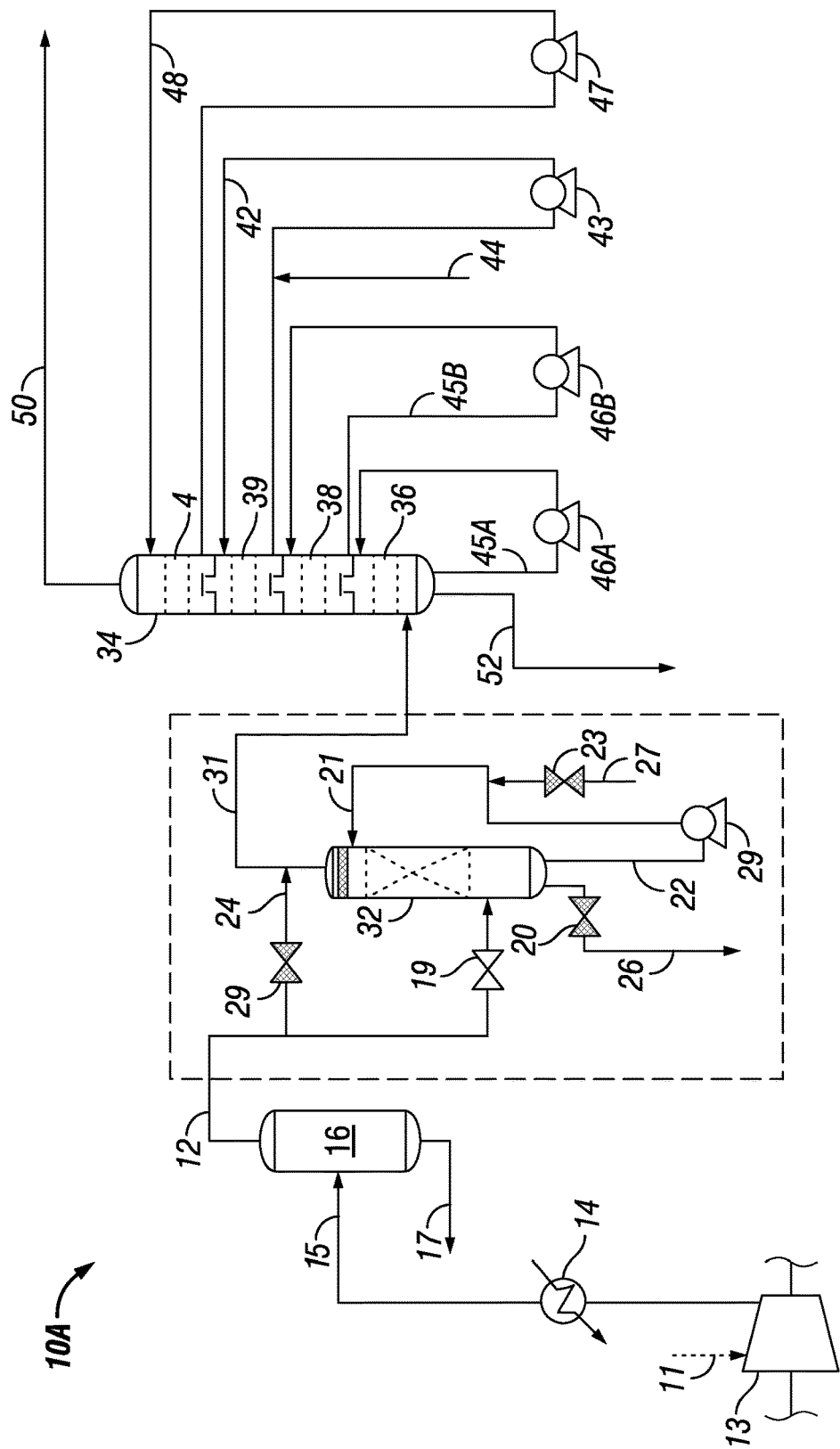
FIG. 1 illustrates an example process for removal of carbonyls from a hydrocarbon stream using standalone carbonyl absorber upstream of the caustic tower.

With reference to FIG. 1, the present disclosure provides a process 10A for treating a hydrocarbon gas stream 11, in accordance with example embodiments. Hydrocarbon gas stream 11 may comprise hydrocarbons, hydrogen sulfide or other sulfur compounds, acetaldehyde, acetone, as well as other acid gas species. Hydrocarbons may be present in an amount of about 60% to about 85% by weight of the hydrocarbon gas stream 11. Sulfur compounds, such as hydrogen sulfide, may be present in an amount of about 20 ppm to about 500 ppm by weight of the hydrocarbon gas stream 11. Acetaldehyde may be present in an amount of about 20 ppm to about 200 ppm by weight of the hydrocarbon gas stream 11. Acetone may be present in an amount of about 5 ppm to about 20 ppm by weight of the hydrocarbon gas stream 11. Other acid gas species, such as for example, $CO_2$ may be present in an amount of about 50 ppm to about 500 ppm by weight of the hydrocarbon gas stream 11. This stream may be located within the compression section of an ethylene plant and may be referred to as "cracked gas" as it is the product of steam cracking. Hydrocarbon gas stream 11 is pressurized in compressor 13 and cooled in an aftercooler 14 prior to acid gas removal in caustic tower 34. Knock-out drum 16 may separate the cooled cracked gas 15 into condensate liquid 17 and vapor stream 12. Knock-out drum 16 may be positioned upstream in the flow stream from that of the caustic tower 34.

A mass transfer device, such as packed column 32, may be positioned between knock-out drum 16 and the caustic tower 34. A liquid bisulfite stream 21 may be pumped to the top of the packed column 32 for intimate counter-contact with vapor stream 12. The liquid bisulfite stream may comprise an alkali metal bisulfite such as sodium bisulfite, potassium bisulfite, other alkali metal bisulfites, and combinations thereof. The alkali metal bisulfite may be present in the liquid bisulfite stream in an amount of about 5% to about 15% by weight of the liquid bisulfite stream. The liquid bisulfite stream may be an aqueous solution that comprises an alkali metal bisulfite and water. In example embodiments, the acetaldehyde content in vapor stream 12 may react with the bisulfite in the liquid bisulfite stream 21 to form an adduct product that may be soluble in the liquid bisulfite stream 21. The overhead hydrocarbon gas stream 31 leaving the packed column may be essentially free of the acetaldehyde, and the bottoms liquid 22 may contain the formed adduct and any unreacted liquid bisulfite. Bottoms liquid 22 may be recirculated back to the top of the column via recirculating pump 28. For example, the acetaldehyde content in overhead hydrocarbon gas stream 31 may be less than about 1 ppm by weight. When the bisulfite content in the recirculating solution reaches about 1% by weight both valves 20 and 23 may be opened to allow addition of fresh bisulfite solution stream 27 through valve 23 and the depleted bisulfite solution stream 26 to discharge from the column through valve 20.

In example embodiments, circulating liquid bisulfite stream 21 in packed column 32 may release small ppm level of sulfur dioxide ($SO_2$) into overhead hydrocarbon gas stream 31. Any $SO_2$ produced may react and be converted to $NaHSO_3$ in the caustic tower 34.

In the illustrated embodiment, a line 24 may provide a bypass for hydrocarbon gas stream 11 around packed column 32. Valve 19 may normally be open while a valve 29 may normally be closed so that hydrocarbon gas stream 11 flows through packed column 32.

Overhead hydrocarbon gas stream 31 may be introduced to caustic tower 34 to remove remaining acid gas components. For example, caustic tower 34 may remove essentially all of the remaining acid gas components from hydrocarbon gas stream 31. Caustic tower 34 may comprise a plurality of sections including, but not limited to, bottom section 36, which may receive overhead hydrocarbon gas stream 31, a middle section 38, a top section 39, and water wash section 40. A strong caustic solution circuit 42 may receive an addition of fresh make-up caustic 44 as required when the concentration of caustic in weak caustic circuit 45A drops below a pre-determined level of 1% to 2% NaOH by weight. Make-up caustic solution 44 may comprise 8% to 12% NaOH by weight. Strong caustic solution pump 43 may circulate the strong caustic in the caustic tower 34. Strong caustic solution circuit 42 may connect to caustic tower 34 in any way. In one example, as shown in FIG. 1, strong caustic solution circuit 42 may connect to top section 39. FIG. 1 shows only one connection to caustic solution circuit 42 but it may connect anywhere and to multiple sections. As mentioned above, caustic tower 34 may comprise a plurality of sections. The number of sections may depend on the acid gas concentration in hydrocarbon gas stream 31 to the caustic tower among other variables. The caustic tower may further comprise a plurality of pumps and side streams. A plurality of side stream pumps 46A-B may draw off liquids at various points in caustic tower 34 through a plurality of side streams 45A-B and return the liquids at a different point in caustic tower 34. A weak or tower spent caustic bleed stream 52 may be withdrawn from caustic tower 34. After passing though caustic tower 34, overhead hydrocarbon gas stream 31 may be substantially depleted of acid gases to the required levels in treated hydrocarbon gas stream 50. Treated hydrocarbon gas stream 50 may comprise less than 1 vppm $CO_2$ and less than 0.1 vppm $H_2S$ (vppm meaning volume part per million). In accordance with present embodiments, treated hydrocarbon gas stream 50 may be essentially free of carbonyl content, for example, carbonyls may be present in an amount less than about 1 ppm by weight.

Overhead hydrocarbon gas stream 31 may travel through caustic tower 34 and contact strong caustic which may reduce the concentration of acid gas components. Hydrocarbon gas stream 31 may travel to top section 40, where the stream may be contacted with water provided from wash water circuit 48. Contacting overhead hydrocarbon gas stream 31 with water may remove entrained caustic droplets from the hydrocarbon gas stream. Pump 47 may circulate wash water through top section 40.

Figure 2:
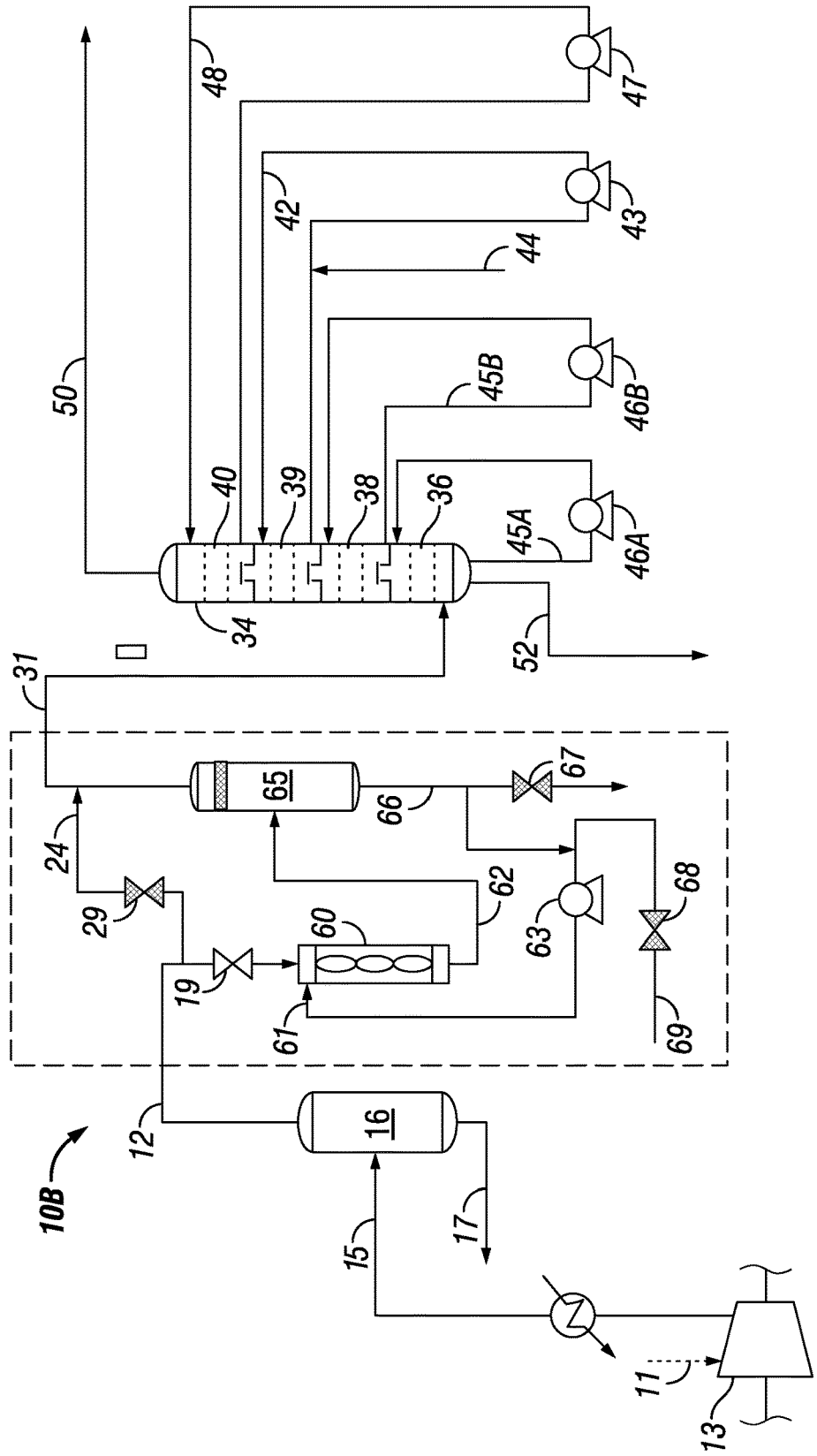
FIG. 2 illustrates another example process for removal of carbonyls from a hydrocarbon stream using static mixer absorber upstream of the caustic tower.

FIG. 2 illustrates an alternative embodiment 10B for treating hydrocarbon gas stream 11. As discussed above, hydrocarbon gas stream 11 may comprise hydrocarbons, hydrogen sulfide or other sulfur compounds, acetaldehyde, acetone, as well as other acid gas species such as $CO_2$. As illustrated, the configuration of the compressor 13, knock-out drum 16, aftercooler 14, and caustic tower 34 may be the same as in FIG. 1. In the illustrated embodiment, the packed column of FIG. 1 may be replaced by another mass transfer device, such as an inline static mixer 60. A liquid bisulfite stream 61 may be introduced into static mixer 60 which may contact vapor stream 12. The liquid bisulfite stream 61 may comprise an alkali metal bisulfite such as sodium bisulfite, potassium bisulfite, other alkali metal bisulfites, and combinations thereof. Static mixer 60 may thoroughly mix the vapor stream 12 and liquid bisulfite stream 61 to form a gas-liquid mixture stream 62. The mixing of vapor stream 12 and liquid bisulfite stream 61 may facilitate a reaction between acetaldehyde and other carbonyls that may be present in vapor stream 12 and bisulfite. The reaction product may be a soluble adduct. The gas-liquid mixture stream may comprise the adduct and unreacted liquid bisulfite. Gas-liquid mixture stream 62 may be introduced into knock-out drum 65 where a liquid bottoms 66 and overhead hydrocarbon gas stream 31 may be separated.

A line 24 may provide a bypass for vapor stream 12 around static mixer 60. Valve 19 may be normally open while a valve 29 may be normally closed so that vapor stream 12 flows through static mixer 60. Pump 63 may recirculate liquid bottoms 66. When the concentration of bisulfite in liquid bisulfite stream 61 reaches about 1% by weight both valves 67 and 68 may be opened to allow addition of fresh bisulfite solution stream 69 through valve 68 and the liquid bottoms 66 to discharge through valve 67.

Overhead hydrocarbon stream 31 may be essentially free of acetaldehyde and may be introduced into caustic tower 34. For example, the acetaldehyde content in overhead hydrocarbon gas stream 31 may be less than about 1 ppm by weight. Caustic tower 34 may be operated in the same manner as described above for caustic tower 34 of FIG. 1. The treated hydrocarbon gas stream 50 may exit the caustic tower 34. In accordance with example embodiments, treated hydrocarbon gas stream 50 may be essentially free of carbonyl content, for example, carbonyls may be present in an amount less than about 1 ppm by weight.

Figure 3:
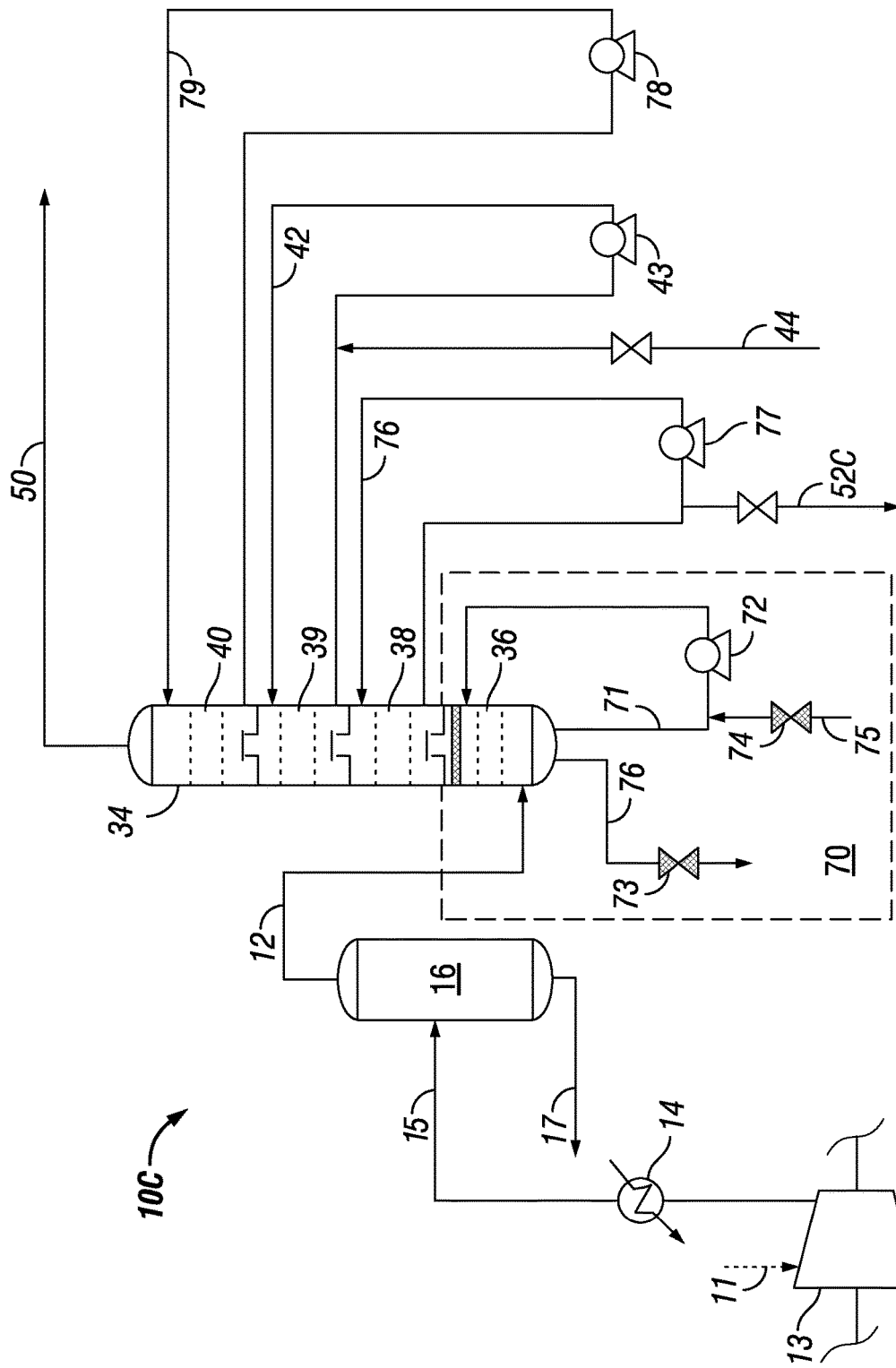
FIG. 3 illustrates yet another example process for removal of carbonyls from a hydrocarbon stream placing the carbonyl absorber at the bottom of the caustic tower, as part of the tower.

Another alternate embodiment for removal of acetaldehyde is shown in FIG. 3. The illustrated embodiment may be applicable for both new construction and existing caustic towers, for example, with 3 or more caustic sections and water wash section. In accordance with example embodiments, the bottom caustic section may be converted to be used as bisulfite treatment section and using the remaining two or more caustic sections for acid gas removal.

Referring to FIG. 3, the present disclosure provides a process 10C for treating vapor stream 12. Vapor stream 12 may comprise hydrocarbons, hydrogen sulfide or other sulfur compounds, acetaldehyde, acetone, as well as other acid gas species such as $CO_2$. As illustrated, the configuration of the compressor 13, knock-out drum 16, aftercooler 14 may be the same as in FIG. 1. Vapor stream 12 may be directed to caustic tower 34. The bottom section 36 may act as a mass transfer device and recirculate a liquid bisulfite stream 70. The liquid bisulfite stream 70 and vapor stream 12 may contact causing a reaction between acetaldehyde that may be present in the vapor stream 12 and the bisulfite to form a soluble adduct. The gas may flow upward leaving bottom section 36 through a chimney tray separating bottom section 36 and middle section 38. The gas flowing upward from the bottom section 36 may be essentially free of acetaldehyde, for example, containing no more than about 1 ppm by weight acetaldehyde. The liquid bottoms 71 may comprise the soluble adduct and unreacted bisulfite. The liquid bottoms 71 may be recirculated back into bottom section 36 by pump 72. When the bisulfite content in the recirculating solution reaches about 1% by weight both valves 73 and 74 may open to allow addition of fresh bisulfite solution stream 75 through valve 74 and the depleted bisulfite solution stream 76 to leave caustic tower 34 through valve 73.

Acetaldehyde free hydrocarbon gas leaving bottom section 36 may contact a weak caustic solution in middle section 38. The weak caustic may comprise 1-2% NaOH, 3-4% $Na_2CO_3$, and 2-3% by weight $Na_2S$. The weak and strong caustic sections may remove essentially all of the remaining acid gas components. The caustic treating sections in caustic tower 34 may comprise a weak caustic solution in middle section 38, a strong caustic solution in top section 39, and a water solution in water wash section 40. The strong caustic may comprise 8-12% by weight NaOH. A strong caustic solution circuit 42 may receive an addition of fresh make-up caustic 44 as required for the removal of acid gases from vapor stream 12 to the required levels in treated hydrocarbon gas stream 50. The strong caustic solution may be circulated by a pump 43 to top section 39. A weak or tower spent caustic solution circuit 76 may be circulated by a pump 77 in middle section 38. Additionally, a weak or spent caustic stream 52C may be withdrawn from spent caustic solution circuit 76.

Hydrocarbon gas may flow up through the tower and contacts a strong caustic in strong section 39. The strong caustic solution may further reduce the concentration of acid gas components in the hydrocarbon gas. The hydrocarbon gas may rise into top section 40, where a wash water circuit 79 may provide water for contacting with the hydrocarbon gas. The contacting may remove entrained caustic droplets from the hydrocarbon gas in the tower. Treated hydrocarbon gas stream may leave top section 40 with reduced acid gas content. The acid gas may be less than 1 vppm $CO_2$ and less than 0.1 vppm $H_2S$ (vppm, meaning volume part per million).

While the preceding description is directed to acetaldehyde removal it should understood that the techniques described herein may also be useful for removal of other carbonyls from hydrocarbon gas streams, such as cracked gas streams. For example, the disclosed techniques may be used for removal of aldehydes, ketones, carboxylic acids, esters, and amides from gas streams. Additionally, while the present disclose is directed to removal of acetaldehyde and other carbonyls from hydrocarbon gas streams, one of ordinary skill in the art would appreciate that alkali metal bisulfites may be used for removal of carbonyls from a wide variety of gas streams where such removal may be beneficial. One example may include removal of carbonyls (e.g., aldehydes and other carbonyls) during the production of ethylene and propylene with oxygenated feedstock; such has methanol to olefins (MTO), and alcohol dehydration. By way of example, use of alkali metal bisulfites for carbonyl removal may also reduce drawbacks from inclusion of carbonyls in a caustic scrubber operating with the effluent of MTO or alcohol dehydration.

EXAMPLES

To facilitate a better understanding of the present embodiments, the following examples of some illustrative embodiments are given. In no way should such examples be read to limit, or to define the scope of the disclosure.

The acetaldehyde removal from gas phase hydrocarbon stream provided by the present invention is further illustrated by the following examples wherein all percentages are by weight unless specified otherwise. A gas chromatography (GC) method was used to evaluate the composition of acetaldehyde in the hydrocarbon stream. Gas samples were collected by filling sample bags from the absorption column overhead outlet. Each sample was then analyzed by GC to determine the amount of acetaldehyde in the hydrocarbon gas.

The Absorption Column consisted of 1 inch (2.54 cm) inside diameter stainless steel column, packed with 0.24 inch (6.1 mm) Propak stainless steel packing to a height of 36 inches (91.44 cm). Sodium bisulfite solution is allowed to flow down the column packing contacting counter currently against the up flowing propane-propylene mixture gas that contained 200 wppm acetaldehyde. The 20 wt % propane and 80 wt % propylene with 200 wppm acetaldehyde gas mixture was purchased in cylinders. The concentration of acetaldehyde was checked in the laboratory CG to be 199 wppm.

The absorption column is operated at 10 psig (0.69 barg) and temperature of 95° F. (35° C.). Temperatures below 50° C. are well suited for the reaction of sodium bisulfite with acetaldehyde to form solid adduct that is soluble in the aqueous phase.

The gas flow rate to the bottom of the absorption column was targeted at 52 liters/min measured at the operating conditions by a calibrated gas meter; while the liquid bisulfite solution flow to the top of the column was targeted at 18.5 cc/min; such flow rates to the column were calculated for operation well below the flooding regime of the packing.

Example 1

The absorption column operated with propane-propylene gas mixture containing 199 wppm acetaldehyde fed to the bottom of the column, and contacted counter-currently with 10 wt % sodium bisulfite solution fed to the top of the packing. The acetaldehyde reacted totally with the sodium bisulfite solution which formed an adduct soluble in the liquid solution. Thus, the acetaldehyde was depleted from the gas phase and at the column outlet (exit gas) stream the concentration of the acetaldehyde measured less than 1 wppm, which is the limit of detection of the GC.

Density of liquid sodium bisulfite solution samples for fresh sample, sample #1 and sample #2 measured at 9.22, 10.10, and 10.19 wt % sodium bisulfite; this concentration effect is due to evaporation of water into the dry propane-propylene gas feed. Data of Example 1 are shown in Table 1.

TABLE 1

| Run Time minutes | Bisulfite Solution Inlet, ° F. | Condenser Out, ° F. | Rx Press (Out) psi | Gas meter Inlet, ° F. | Gas Rate L/min | Bisulfite rate, cc/min | Exit Acet Conc, wppm | Comments |
|---|---|---|---|---|---|---|---|---|
| 0 | 93 | 88 | 8 | 96 | 17.78 | 20 | | start bisulfite pump spent bisulfite draining, start C3 flow |
| 3 | 92 | 88 | 10 | 95 | 17.62 | 47 | | |
| 13 | 99 | 96 | 10 | 95 | 17.88 | 48 | | |
| 23 | 93 | 91 | 10 | 93 | 21.33 | 51 | | |
| 36 | 93 | 88 | 9 | 93 | 21.28 | 56 | | spent bisulfite Sample #1 |
| 45 | 93 | 88 | 9 | 94 | 18.44 | 51 | | |
| 47 | 93 | 88 | 9 | 94 | 18.00 | 61 | 2 | Gas Sample #1 |
| 65 | 97 | 95 | 9 | 95 | 19.75 | 28 | | bisulfite suction tube above liquid |
| 73 | 94 | 88 | 10 | 96 | 18.48 | 16 | <1 | Gas Sample #2 |
| 93 | 95 | 89 | 10 | 94 | 19.59 | 54 | <1 | Gas Sample #3 |
| 108 | 95 | 89 | 10 | 94 | 19.49 | 54 | | spent bisulfite Sample #2 |
| 123 | 96 | 90 | 10 | 94 | 19.67 | 54 | <1 | Gas Sample #4 |
| 138 | 96 | 88 | 10 | 94 | 19.59 | 54 | <1 | Gas Sample #5 |
| 145 | | | | | | | | Shut Down |

Notes
(1) Feed Bisulfite Solution 9.22 wt % sodium bisulfite
(2) Spent Bisulfite Solution #1 10.10 wt % sodium bisulfite
(3) Spent Bisulfite Solution #2 10.19 wt % sodium bisulfite Example 2

Same absorber column operated at the same conditions and gas and liquid rates as in example 1, but the concentration of the liquid solution is decreased to 5 wt % sodium bisulfate solution fed to the top of the packing. The acetaldehyde similarly was depleted from the gas phase and at the column outlet (exit gas) stream the concentration of the acetaldehyde measured less than 1 wppm, which is the limit of detection of the GC. Data of Example 2 are shown in Table 2.

TABLE 2

| Run Time minutes | Bisulfite Solution Inlet, ° F. | Condenser Out, ° F. | Rx Press (Out) psi | Gas meter Inlet, ° F. | Gas Rate L/min | Bisulfite rate, cc/min | Exit Acet Conc, wppm | Comments |
|---|---|---|---|---|---|---|---|---|
| 0 | 93 | 88 | 9 | 94 | 18.0 | 20 | | start bisulfite pump spent bisulfite draining, start C3 flow |
| 35 | 93 | 88 | 9 | 94 | 18.44 | 51 | | |
| 45 | 93 | 88 | 10 | 94 | 18.00 | 51 | <1 | Gas Sample #1 |

TABLE 2-continued

| Run Time minutes | Bisulfite Solution Inlet, °F. | Condenser Out, °F. | Rx Press (Out) psi | Gas meter Inlet, °F. | Gas Rate L/min | Bisulfite rate, cc/min | Exit Acet Conc, wppm | Comments |
|---|---|---|---|---|---|---|---|---|
| 70 | 93 | 88 | 10 | 96 | 18.5 | 55 | <1 | Gas Sample #2 |
| 80 | | | | | | | | Shut Down |

Example 3

Same absorption column operated at the same conditions and gas and liquid rates as in example 1 but the concentration of the liquid solution is decreased to 1 wt % sodium bisulfite solution fed to the top of the packing. The acetaldehyde similarly was depleted from the gas phase and at the column outlet (exit gas) stream the concentration of the acetaldehyde measured less than 3 wppm. Data of Example 3 are shown in Table 3

TABLE 3

| Run Time minutes | Bisulfite Solution Inlet, °F. | Condenser Out, °F. | Rx Press (Out) psi | Gas meter Inlet, °F. | Gas Rate L/min | Bisulfite rate, cc/min | Exit Acet Conc, wppm | Comments |
|---|---|---|---|---|---|---|---|---|
| 0 | 93 | 89 | 10 | 94 | 18.05 | 45 | | start bisulfite pump spent bisulfite draining, start C3 flow |
| 30 | 94 | 88 | 10 | 95 | 18.14 | 48 | | |
| 48 | 93 | 89 | 10 | 95 | 18.70 | 52 | 2.1 | Gas Sample #1 |
| 72 | 94 | 88 | 10 | 96 | 18.55 | 53 | 2.6 | Gas Sample #2 |
| 88 | | | | | | | | Shut Down |

SUMMARY OF RESULTS

Results of the Examples 1, 2 and 3 shows that removal of acetaldehyde is almost complete when using 10 and 5 wt. % sodium bisulfite solution. While when the sodium bisulfite solution reaches one weight percent in the absorption column the removal of acetaldehyde from the hydrocarbon gas stream reaches 98.5%.

TABLE 4

| Example # | Bisulfite wt % | Inlet Acetaldehyde Conc. wppm | Exit Acetaldehyde Conc, wppm |
|---|---|---|---|
| 1 | 10 | 199 | <1 (Detection Limit) |
| 2 | 5 | 199 | <1 (Detection Limit |
| 3 | 1 | 199 | <3 |

For the sake of brevity, only certain ranges are explicitly disclosed herein. However, ranges from any lower limit may be combined with any upper limit to recite a range not explicitly recited, as well as, ranges from any lower limit may be combined with any other lower limit to recite a range not explicitly recited, in the same way, ranges from any upper limit may be combined with any other upper limit to recite a range not explicitly recited. Additionally, whenever a numerical range with a lower limit and an upper limit is disclosed, any number and any included range falling within the range are specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values even if not explicitly recited. Thus, every point or individual value may serve as its own lower or upper limit combined with any other point or individual value or any other lower or upper limit, to recite a range not explicitly recited.

Although the present invention and its advantages have been described in detail, it should be understood that various changes, substitutions and alterations may be made herein without departing from the spirit and scope of the invention as defined by the appended claims. While apparatus and methods are described in terms of "comprising," "containing," "having," or "including" various components or steps, the apparatus and methods can also "consist essentially of" or "consist of" the various components and steps.

What is claimed is:

1. A method for removal of carbonyls comprising:
   steam cracking a hydrocarbon gas stream to produce a cracked hydrocarbon gas stream wherein the cracked hydrocarbon gas stream comprises a concentration of about 20 ppm to about 500 ppm acetaldehyde and about 5 ppm to about 20 ppm acetone;
   introducing the cracked hydrocarbon gas stream into a multi-stage gas compression system;
   drawing a compressed cracked hydrocarbon gas stream from an inter-stage location in the multi-stage gas compression system;
   introducing the compressed cracked hydrocarbon gas stream into a bottom of a gas-liquid absorber;
   circulating an aqueous alkali metal bisulfite stream through the gas-liquid absorber such that the aqueous alkali metal bisulfite stream and the compressed cracked hydrocarbon gas stream are counter currently contacted wherein the acetaldehyde and acetone are extracted into and reacted with the aqueous alkali metal bisulfite in solution and an overhead hydrocarbon gas stream exiting the gas-liquid absorber has a concentration of acetaldehyde and a concentration of acetone of less than about 1 ppm each; and
   sending the overhead hydrocarbon gas stream to a caustic tower.

2. The method of claim 1 wherein the cracked gas stream further comprises a concentration of about 20 ppm to about 500 ppm $H_2S$ and about 50 ppm to about 500 ppm $CO_2$.

3. The method of claim 1 wherein the compressed cracked hydrocarbon gas stream is at a pressure of about 10 atm to about 20 atm.

4. The method of claim 1, wherein the compressed cracked hydrocarbon gas stream is introduced into a knock-out drum to separate a condensate liquid before the step of introduction into the gas-liquid absorber.

5. The method of claim 1, wherein the gas-liquid absorber is a column and wherein the column comprises packing or trays.

6. The method of claim 1, wherein the gas-liquid absorber is a bottoms section of the caustic tower.

7. The method of claim 1, wherein the aqueous alkali metal bisulfite is selected from the group consisting of sodium bisulfite, potassium bisulfite, magnesium bisulfite, strontium bisulfite, and combinations thereof.

8. The method of claim 1, wherein the alkali metal bisulfite is present in the aqueous alkali metal bisulfite stream in an amount of about 5% to about 15% by weight.

9. The method of claim 1 wherein the step of circulating comprises:
drawing a bottoms stream of aqueous alkali metal bisulfite; and
pumping the bottoms stream of aqueous alkali metal bisulfite to a top of the gas-liquid absorber.

10. The method of claim 1 further comprising:
stopping circulating the aqueous alkali metal bisulfite stream when a concentration of alkali metal bisulfite in solution reaches about 1% by weight;
draining the aqueous alkali metal bisulfite stream from the gas-liquid absorber to produce a spent aqueous alkali metal bisulfite stream; and
adding a fresh alkali metal bisulfite stream to the gas-liquid absorber.

11. The method of claim 10 further comprising:
heating the spent aqueous alkali metal bisulfite stream to a temperature of above 100° C.; and
stripping the spent aqueous alkali metal bisulfite stream to produce the fresh alkali metal bisulfite stream.

12. The method of claim 1 further comprising counter currently contacting the overhead hydrocarbon gas stream with caustic solution in the caustic tower.

13. A method for removal of carbonyls comprising:
cracking a hydrocarbon gas stream in the presence of steam to produce a cracked hydrocarbon gas stream wherein the cracked hydrocarbon gas stream comprises a concentration of about 20 ppm to about 500 ppm acetaldehyde and about 5 ppm to about 20 ppm acetone;
introducing the cracked hydrocarbon gas stream into a multi-stage gas compression system wherein the cracked hydrocarbon gas stream is compressed to about 10-20 atm to form a compressed cracked hydrocarbon gas stream;
drawing the compressed cracked hydrocarbon gas stream from an inter-stage location in the multi-stage gas compression system and introducing the compressed cracked hydrocarbon gas stream into a bottom of a gas-liquid absorber;
circulating an aqueous sodium bisulfite stream comprising about 5% to about 15% sodium bisulfite by weight through the gas-liquid absorber such that the aqueous sodium bisulfite stream and the compressed cracked hydrocarbon gas stream are counter currently contacted;
extracting at least a portion of the acetaldehyde and acetone into the aqueous sodium bisulfite stream;
reacting the acetaldehyde and acetone with the aqueous alkali metal bisulfite in solution;
producing an overhead hydrocarbon gas stream exiting the gas-liquid absorber that has a concentration of acetaldehyde and a concentration of acetone of less than about 1 ppm each; and
sending the overhead hydrocarbon gas stream to a caustic tower.

14. The method of claim 13 wherein the overhead hydrocarbon gas stream is counter currently contacted with a caustic solution in the caustic tower.

15. The method of claim 13 wherein the caustic tower is either a trayed or a packed tower comprising a weak caustic section, a strong caustic section, and a water wash section.

16. The method of claim 15 wherein the weak caustic section counter currently contacts the overhead hydrocarbon gas stream with a weak caustic solution comprising at least one caustic agent selected from the group consisting of NaOH, $Na_2CO_3$, $Na_2S$, and combinations thereof.

17. The method of claim 16 wherein the weak caustic solution comprises 1-2% NaOH, 3-4% $Na_2CO_3$, and 2-3% $Na_2S$ by weight.

18. The method of claim 16 wherein the strong caustic section counter currently contacts the overhead hydrocarbon gas stream with a caustic solution comprising about 8-12% by weight NaOH.

19. The method of claim 16 wherein the overhead hydrocarbon gas stream comprises entrained caustic droplets and the water wash section removes at least a portion of entrained caustic droplets.

* * * * *